United States Patent
Yifat et al.

(10) Patent No.: US 12,011,306 B2
(45) Date of Patent: Jun. 18, 2024

(54) PATIENT HEAD PROTECTION DEVICE

(71) Applicant: Radiaction Ltd, Tel Aviv (IL)

(72) Inventors: Jonathan Yifat, Ramat Hasharon (IL);
Yossi Bar, Bern (CH); Amir Belson, Savyon (IL)

(73) Assignee: Radiaction Ltd, Tel Aviv (IL)

( * ) Notice: Subject to any disclaimer, the term of this patent is extended or adjusted under 35 U.S.C. 154(b) by 615 days.

(21) Appl. No.: 16/731,548

(22) Filed: Dec. 31, 2019

(65) Prior Publication Data

US 2020/0205754 A1 Jul. 2, 2020

Related U.S. Application Data

(60) Provisional application No. 62/787,653, filed on Jan. 2, 2019.

(51) Int. Cl.
*A61B 6/10* (2006.01)
*A61B 6/04* (2006.01)
*A61B 90/00* (2016.01)

(52) U.S. Cl.
CPC ............ *A61B 6/102* (2013.01); *A61B 6/0407* (2013.01); *A61B 2090/033* (2016.02)

(58) Field of Classification Search
CPC ..... A61B 6/10; A61B 90/10; A61B 2090/103; A61B 6/102; A61B 6/0407; A61G 13/121
See application file for complete search history.

(56) References Cited

U.S. PATENT DOCUMENTS

| | | | |
|---|---|---|---|
| 2,593,526 A | 4/1952 | Savage |
| 2,835,824 A | 5/1958 | Schepker |
| 3,310,053 A | 3/1976 | Greenwood |
| 3,967,129 A | 6/1976 | Winkler |

(Continued)

FOREIGN PATENT DOCUMENTS

| | | |
|---|---|---|
| CN | 1278713 A | 1/2001 |
| CN | 1331956 A | 1/2002 |

(Continued)

OTHER PUBLICATIONS

International Search Report and Written Opinion for PCT/US2019/069162 dated Apr. 2, 2020.

(Continued)

*Primary Examiner* — Angela M Hoffa
*Assistant Examiner* — Younhee Choi
(74) *Attorney, Agent, or Firm* — Shay Glenn LLP

(57) ABSTRACT

The present invention relates, in some embodiments thereof, to devices and methods for protecting a patient's upper body portion from collision with medical instruments, such as an X-ray imaging system and/or an X-ray radiation protection apparatus. In some embodiments, the invention provides a head protection device comprising a support platform for supporting a patient's head; and a head protection shield connected to the support platform. In some embodiments, the shield is pivotally connected to the support platform to allow a relative pivotal movement between the support platform and the shield. In some embodiments, the device includes an adjuster unit allowing to vertically adjust the distance between the head protector shield and the support platform, thereby allowing to fit various head sizes.

21 Claims, 10 Drawing Sheets

(56) References Cited

U.S. PATENT DOCUMENTS

| | | |
|---|---|---|
| 3,984,695 A | 10/1976 | Collica et al. |
| 3,984,696 A | 10/1976 | Collica et al. |
| 4,034,228 A | 7/1977 | Arauner |
| 4,062,518 A | 12/1977 | Stivender et al. |
| 4,122,350 A | 10/1978 | Lipthay et al. |
| 4,140,129 A | 2/1979 | Heinz et al. |
| 4,210,811 A | 7/1980 | Dennhoven et al. |
| 4,400,820 A | 8/1983 | O'Dell et al. |
| 4,581,538 A | 4/1986 | Lenhart |
| 4,587,277 A | 5/1986 | Sato |
| 4,795,654 A | 1/1989 | Teleki |
| 4,837,796 A | 6/1989 | Ema |
| 4,938,233 A | 7/1990 | Orrison, Jr. |
| 4,969,170 A | 11/1990 | Kikuchi et al. |
| 4,977,585 A | 12/1990 | Boyd |
| 5,006,718 A | 4/1991 | Lenhart |
| 5,099,134 A | 3/1992 | Hase |
| 5,299,243 A | 3/1994 | Picco |
| 5,335,366 A | 8/1994 | Daniels |
| 5,417,225 A | 5/1995 | Rubenstein et al. |
| 5,438,705 A | 8/1995 | Mendez et al. |
| 5,523,578 A | 6/1996 | Herskovic |
| 5,525,408 A | 6/1996 | Weir et al. |
| 5,570,770 A | 11/1996 | Baaten et al. |
| 5,651,044 A | 7/1997 | Klotz, Jr. et al. |
| 5,769,816 A | 6/1998 | Barbut et al. |
| 5,769,819 A | 6/1998 | Schwab et al. |
| 5,848,449 A * | 12/1998 | Hauger ............... A61B 6/0421 5/601 |
| 5,900,638 A | 5/1999 | Jaeger et al. |
| 5,937,028 A | 8/1999 | Tybinkowski et al. |
| 5,947,981 A | 9/1999 | Cosman |
| 5,981,964 A | 11/1999 | Mcauley et al. |
| 6,003,174 A | 12/1999 | Kantrowitz et al. |
| 6,083,239 A | 7/2000 | Addis |
| 6,120,534 A | 9/2000 | Ruiz |
| 6,139,517 A | 10/2000 | Macoviak et al. |
| 6,245,012 B1 | 6/2001 | Kleshinski |
| 6,254,563 B1 | 7/2001 | Macoviak et al. |
| 6,254,633 B1 | 7/2001 | Pinchuk et al. |
| 6,258,120 B1 | 7/2001 | McKenzie et al. |
| 6,281,515 B1 | 8/2001 | Demeo et al. |
| 6,325,538 B1 | 12/2001 | Heesch |
| 6,352,363 B1 | 3/2002 | Munger et al. |
| 6,361,545 B1 | 3/2002 | Macoviak et al. |
| 6,371,935 B1 | 4/2002 | Macoviak et al. |
| 6,448,571 B1 | 9/2002 | Goldstein |
| 6,456,684 B1 | 9/2002 | Mun et al. |
| 6,459,091 B1 | 10/2002 | Demeo et al. |
| 6,481,888 B1 | 11/2002 | Morgan |
| 6,499,487 B1 | 12/2002 | McKenzie et al. |
| 6,537,297 B2 | 3/2003 | Tsugita et al. |
| 6,547,760 B1 | 4/2003 | Samson et al. |
| 6,636,757 B1 | 10/2003 | Jascob et al. |
| 6,653,648 B2 | 11/2003 | Goldstein |
| 6,674,087 B2 | 1/2004 | Cadwalader et al. |
| 6,692,513 B2 | 2/2004 | Streeter et al. |
| 6,703,632 B1 | 3/2004 | Macklis et al. |
| 6,709,415 B2 | 3/2004 | Navia et al. |
| 6,712,834 B2 | 3/2004 | Yassour et al. |
| 6,718,008 B1 | 4/2004 | He et al. |
| 6,828,578 B2 | 12/2004 | Demeo et al. |
| 6,841,791 B2 | 1/2005 | Demeo et al. |
| 7,029,175 B2 | 4/2006 | Karaus et al. |
| 7,044,958 B2 | 5/2006 | Douk et al. |
| 7,057,194 B2 | 6/2006 | Goldstein |
| 7,091,508 B2 | 8/2006 | Goldstein |
| 7,108,422 B2 | 9/2006 | Borom |
| 7,196,023 B2 | 3/2007 | Langley et al. |
| 7,232,453 B2 | 6/2007 | Shimon |
| 7,294,845 B2 | 11/2007 | Ballsieper |
| 7,331,712 B2 | 2/2008 | Fischer et al. |
| 7,391,042 B2 | 6/2008 | Goldstein |
| 7,420,193 B2 | 9/2008 | Treuth |
| 7,440,539 B2 | 10/2008 | Danielsson et al. |
| 7,441,954 B2 | 10/2008 | Bernhardt |
| 7,465,947 B2 | 12/2008 | Magram |
| 7,537,600 B2 | 5/2009 | Eskuri |
| 7,648,273 B2 | 1/2010 | Manzke et al. |
| 7,829,873 B2 | 11/2010 | Fox et al. |
| 7,837,385 B2 | 11/2010 | Klingenbeck-Regn |
| 7,857,512 B2 | 12/2010 | Camus |
| 7,897,949 B2 | 3/2011 | Ballsieper |
| 8,052,717 B2 | 11/2011 | Mujkanovic |
| 8,113,713 B2 | 2/2012 | Belson et al. |
| 8,114,114 B2 | 2/2012 | Belson |
| 8,123,779 B2 | 2/2012 | Demond et al. |
| 8,298,258 B2 | 10/2012 | Anderson et al. |
| 8,337,519 B2 | 12/2012 | Wasicek |
| 8,382,788 B2 | 2/2013 | Galdonik et al. |
| 8,420,902 B2 | 4/2013 | Gilsinger |
| 8,439,564 B2 | 5/2013 | Belson et al. |
| 8,460,777 B2 | 6/2013 | Long |
| 8,639,564 B2 | 1/2014 | Toebes et al. |
| 8,740,930 B2 | 6/2014 | Goodwin |
| 8,903,038 B2 | 12/2014 | Matsuzawa et al. |
| 8,968,354 B2 | 3/2015 | Wang et al. |
| 9,038,219 B2 | 5/2015 | Gross et al. |
| 9,144,485 B2 | 9/2015 | Bergheim |
| 9,370,331 B2 | 6/2016 | Belson et al. |
| 9,492,265 B2 | 11/2016 | Russell et al. |
| 9,744,023 B2 | 8/2017 | Wang et al. |
| 9,877,821 B2 | 1/2018 | Russell et al. |
| 10,617,509 B2 | 4/2020 | Kleshinski et al. |
| 10,709,395 B2 | 7/2020 | Stegehuis et al. |
| 11,076,819 B2 | 8/2021 | Belson et al. |
| 11,152,128 B2 | 10/2021 | Yifat et al. |
| 11,179,287 B1 * | 11/2021 | Mirbahaeddin ........ A61G 15/10 |
| 11,399,927 B2 | 8/2022 | Kleshinski et al. |
| 11,547,375 B2 | 1/2023 | Yifat et al. |
| 11,621,096 B2 | 4/2023 | Yifat et al. |
| 11,744,529 B2 | 9/2023 | Yifat et al. |
| 2002/0003854 A1 | 1/2002 | Ivan et al. |
| 2002/0015471 A1 | 2/2002 | Yagi |
| 2002/0048089 A1 | 4/2002 | Brown |
| 2002/0193686 A1 | 12/2002 | Gilboa |
| 2003/0084512 A1* | 5/2003 | Fujita ................. A61B 6/0421 5/601 |
| 2003/0100940 A1 | 5/2003 | Yodfat |
| 2003/0112924 A1 | 6/2003 | Seufert |
| 2003/0174802 A1 | 9/2003 | Hare |
| 2004/0020829 A1 | 2/2004 | Magna et al. |
| 2004/0029998 A1 | 2/2004 | Tomita |
| 2004/0042587 A1 | 3/2004 | Deshpande |
| 2004/0208291 A1 | 10/2004 | Stout |
| 2004/0257744 A1 | 12/2004 | Bushko et al. |
| 2005/0010246 A1 | 1/2005 | Streeter et al. |
| 2005/0070779 A1 | 3/2005 | Singh B et al. |
| 2005/0213713 A1 | 9/2005 | Cadwalader et al. |
| 2005/0236588 A1 | 10/2005 | Ein-Gal |
| 2005/0283186 A1 | 12/2005 | Berreda et al. |
| 2006/0097734 A1 | 5/2006 | Roziere |
| 2006/0251219 A1 | 11/2006 | Cadwalader et al. |
| 2006/0262898 A1 | 11/2006 | Partain et al. |
| 2006/0287668 A1 | 12/2006 | Fawzi et al. |
| 2007/0086570 A1 | 4/2007 | Spahn |
| 2007/0189442 A1 | 8/2007 | Sukovic et al. |
| 2007/0242805 A1 | 10/2007 | Somers |
| 2007/0269012 A1 | 11/2007 | Somers |
| 2008/0119722 A1 | 5/2008 | Swaney |
| 2008/0258929 A1 | 10/2008 | Maschke |
| 2009/0010389 A1 | 1/2009 | Ma et al. |
| 2009/0088327 A1 | 4/2009 | Rigatti et al. |
| 2009/0325172 A1 | 12/2009 | Milton et al. |
| 2010/0010535 A1 | 1/2010 | Mujkanovic |
| 2010/0028885 A1 | 2/2010 | Balasubraman et al. |
| 2010/0061509 A1 | 3/2010 | D'Ambrosio et al. |
| 2010/0094119 A1* | 4/2010 | Yu ..................... A61B 90/17 600/1 |
| 2010/0133450 A1 | 6/2010 | Belson et al. |
| 2010/0163758 A1 | 7/2010 | Kirschenbaum |
| 2010/0312268 A1 | 12/2010 | Belson |
| 2011/0314594 A1* | 12/2011 | Rogers ................. A42B 3/04 2/421 |

(56) References Cited

U.S. PATENT DOCUMENTS

| | | |
|---|---|---|
| 2012/0271340 A1 | 10/2012 | Castellano et al. |
| 2013/0129449 A1 | 5/2013 | Ishikawa |
| 2013/0204113 A1 | 8/2013 | Carmi |
| 2013/0267993 A1 | 10/2013 | Carpenter |
| 2013/0270462 A1 | 10/2013 | Beck |
| 2014/0000091 A1 | 1/2014 | Angel et al. |
| 2014/0029720 A1 | 1/2014 | Osherov et al. |
| 2014/0048730 A1 | 2/2014 | Niedzielski et al. |
| 2014/0214069 A1 | 7/2014 | Franklin |
| 2014/0249568 A1 | 9/2014 | Adams et al. |
| 2014/0275998 A1 | 9/2014 | Elchler et al. |
| 2014/0332701 A1 | 11/2014 | Byers et al. |
| 2014/0334608 A1 | 11/2014 | Mulzer et al. |
| 2015/0006607 A1 | 1/2015 | E |
| 2015/0117615 A1 | 4/2015 | Dirauf et al. |
| 2015/0128727 A1 | 5/2015 | Sattler et al. |
| 2015/0305694 A1 | 10/2015 | Sakata |
| 2015/0359505 A1 | 12/2015 | Hoshino |
| 2015/0366650 A1 | 12/2015 | Zi et al. |
| 2016/0029980 A1 | 2/2016 | Osherov et al. |
| 2016/0038365 A1 | 2/2016 | Conner et al. |
| 2016/0143600 A1 | 5/2016 | Schmidt |
| 2016/0150837 A1 | 6/2016 | Kaforey et al. |
| 2016/0158082 A1 | 6/2016 | Gainor et al. |
| 2016/0193731 A1 | 7/2016 | Sattler et al. |
| 2016/0262708 A1 | 9/2016 | Belson et al. |
| 2016/0286890 A1 | 10/2016 | Morin et al. |
| 2016/0317277 A1 | 11/2016 | Carpenter et al. |
| 2016/0345929 A1 | 12/2016 | Azizian et al. |
| 2017/0220709 A1 | 8/2017 | Wan et al. |
| 2017/0265824 A1* | 9/2017 | Wasson, Jr. ............ A61B 6/107 |
| 2017/0278585 A1 | 9/2017 | Almer et al. |
| 2017/0347978 A1 | 12/2017 | Kuspert |
| 2018/0000431 A1 | 1/2018 | Roth et al. |
| 2018/0029972 A1 | 2/2018 | Daly |
| 2018/0168525 A1 | 6/2018 | Belson et al. |
| 2018/0206970 A1 | 7/2018 | Eggert et al. |
| 2018/0214100 A1 | 8/2018 | Kumar |
| 2018/0227468 A1* | 8/2018 | Pritz ..................... A42B 3/22 |
| 2018/0249972 A1 | 9/2018 | Yifat et al. |
| 2018/0250183 A1 | 9/2018 | Zwierstra et al. |
| 2018/0289342 A1 | 10/2018 | Chandwadkar et al. |
| 2019/0015152 A1 | 1/2019 | Howard et al. |
| 2019/0038377 A1* | 2/2019 | Wortmann ............. A61B 90/18 |
| 2019/0059852 A1* | 2/2019 | Zwierstra ............... A61B 5/065 |
| 2021/0283425 A1* | 9/2021 | Kim ..................... A61N 5/1071 |
| 2021/0321885 A1* | 10/2021 | Zaugg ................... A61B 90/40 |
| 2021/0354610 A1* | 11/2021 | Orrington ............. B60N 2/793 |
| 2021/0369383 A1* | 12/2021 | Pawlowicz ............ A61B 90/05 |
| 2022/0071576 A1 | 3/2022 | Foster et al. |
| 2022/0110594 A1 | 4/2022 | Belson et al. |
| 2022/0117566 A1 | 4/2022 | Yifat et al. |
| 2023/0091397 A1 | 3/2023 | Kleshinski et al. |
| 2023/0181132 A1 | 6/2023 | Yifat et al. |

FOREIGN PATENT DOCUMENTS

| | | |
|---|---|---|
| CN | 1442117 A | 9/2003 |
| CN | 101164637 A | 4/2008 |
| CN | 201216602 Y | 4/2009 |
| CN | 202665566 U | 1/2013 |
| CN | 203303071 U | 11/2013 |
| CN | 203341747 U | 12/2013 |
| CN | 203898342 U | 10/2014 |
| CN | 204016322 U | 12/2014 |
| CN | 103045983 B | 12/2015 |
| CN | 205959627 U | 2/2017 |
| CN | 107224297 A | 10/2017 |
| CN | 108309664 A | 7/2018 |
| DE | 19924914 A1 | 12/2000 |
| DE | 102012212104 A1 | 1/2014 |
| DE | 102013214222 A1 | 1/2015 |
| DE | 102014215448 B3 | 12/2015 |
| EP | 0393214 A1 | 10/1990 |
| EP | 3481301 A1 | 5/2019 |
| FR | 2736256 A1 | 1/1997 |
| JP | H0739805 U | 7/1995 |
| JP | 2001037751 A | 2/2001 |
| JP | 2004506911 A | 3/2004 |
| JP | 2004264207 A | 9/2004 |
| JP | 2005177047 A | 7/2005 |
| JP | 2008079728 A | 4/2008 |
| JP | 2009232339 A | 10/2009 |
| JP | 2011511265 A | 4/2011 |
| JP | 2016107655 A | 6/2016 |
| JP | 2017181375 A | 10/2017 |
| JP | 6391149 B2 | 9/2018 |
| JP | 2019523040 A | 8/2019 |
| JP | 7132854 B2 | 9/2022 |
| JP | 2023158023 A | 10/2023 |
| KR | 20120084574 A | 7/2012 |
| KR | 101218378 B1 | 1/2013 |
| KR | 20150099969 A | 9/2015 |
| WO | WO96/01591 A1 | 1/1996 |
| WO | WO03/073939 A1 | 9/2003 |
| WO | WO2004/019817 A1 | 3/2004 |
| WO | WO2005/102174 A1 | 11/2005 |
| WO | WO2006/026646 A1 | 3/2006 |
| WO | WO2006/092078 A1 | 9/2006 |
| WO | WO2007/060561 A2 | 5/2007 |
| WO | WO2008/140486 A2 | 11/2008 |
| WO | WO-2017083437 A1 | 5/2017 |
| WO | WO2017/116828 A1 | 7/2017 |
| WO | WO2018/007437 A1 | 1/2018 |
| WO | WO2018/232037 A1 | 12/2018 |
| WO | WO2020/142556 A1 | 7/2020 |
| WO | WO-2020142564 A1 | 7/2020 |
| WO | WO2021/003191 A1 | 1/2021 |

OTHER PUBLICATIONS

EP19907635.7 Extended Search Report dated Aug. 23, 2022.

Yifat et al.; U.S. Appl. No. 18/181,532 entitled "Radiation protection apparatus and materials therefor," filed Mar. 9, 2023.

Yifat et al.; U.S. Appl. No. 18/355,680 entitled "Supplementary collision detection and prevention system for a medical imager," filed Jul. 20, 2023.

\* cited by examiner

PATIENT HEAD PROTECTION DEVICE

CROSS-REFERENCE TO RELATED APPLICATIONS

This application claims the benefit of U.S. Provisional No. 62/787,653, filed Jan. 2, 2019, the entire content of which is incorporated herein by reference.

FIELD OF THE INVENTION

The present invention relates, in some embodiments thereof, to devices and methods for protecting a patient's upper body portion from collision with medical instruments, such as an X-ray imaging system and/or an X-ray radiation protection apparatus. In some embodiments, the invention provides a head protection device comprising a support platform for supporting a patient's head; and a head protection shield connected to the support platform. In some embodiments, the shield is pivotally connected to the support platform to allow a relative pivotal movement between the support platform and the shield. In some embodiments, the device includes an adjuster unit allowing to vertically adjust the distance between the head protector shield and the support platform, thereby allowing to fit various head sizes.

BACKGROUND OF THE INVENTION

In medical radiology settings, 3D and 2D images of a body are obtained using a C-arm rotating around a patient. The movement of the C-arm around the patient entails the risk of a collision of the C-arm, in particular of the X-ray detector, with the patient and/or creating a stressful environment for the patient.

The most critical and hazardous collision event is associated with possible harmful collisions of moving parts of the C-arm with a patient's head, especially in events of unexpected patient movements.

In current practice, in order to avoid injury to the patient as a result of a collision with the C-arm, additional sensors are mounted on the X-ray detector and the collimator. When such sensors are activated, the movement of the C-arm is stopped. Nevertheless, if the rotation speeds are increased, such protection is in many cases inefficient.

U.S. Pat. No. 7,857,512 discloses a collision protection device for a patient examination table of a medical X-ray device, comprising: a protective element made of an X-ray transparent/radiolucent material that mechanically shields at least a part of the patient examination table; a feeler; a collision sensor, wherein the collision sensor is arranged in the feeler; and a stand or a base directly connected to the collision protection device that decouples the collision protection device from the patient examination table.

U.S. Pat. No. 9,038,219 discloses a patient support apparatus having a support table, a transfer plate, which is disposed movably in relation to the support table in a direction and on which a patient is supported for a surgical intervention and/or a medical imaging examination, and a surgical head restraint unit, which is disposed on the transfer plate. The patient support apparatus includes a position monitoring apparatus for monitoring and/or checking a position of the surgical head restraint unit.

None of the abovesaid devices affords a head protection device which facilitates head adjustment means and which allows stable and efficient protection of a patient's head and neck. Therefore, there is a need of a device for protecting the head of a user. The device should include a shield to cover the face and/or neck, a support platform to support the head, and means to move the shield pivotably over the face. There is an unmet and continuous need in collision protection devices for assuring simple and reliable avoidance of collisions between moving parts of a medical fluoroscopy X-ray device and a patient.

SUMMARY OF THE INVENTION

Objects of the invention are achieved by providing head protection devices and systems for protecting an upper body portion (i.e., the head or face and optionally the neck) of a patient in the process of X-ray imaging.

An aspect of the invention pertains to a patient protection shield in accordance with the disclosure herein below. An aspect of the invention pertains to a method of shielding a patient in accordance with the disclosure herein below.

An aspect of the invention pertains to a medical device including a head protection shield in accordance with the disclosure herein above.

An aspect of the invention pertains to a patient head collision protection device, comprising:
a support platform; and
a head protection shield connected to the support platform and enclosing a space for accommodating a patient's head.

An aspect of the invention pertains to a patient head protection device, comprising:
a head protection shield;
an adjuster unit allowing vertical adjustment of the shield relative to a patient's head platform;
wherein the adjuster unit allows to adjust the space enclosed between the head protection shield and the patient's head platform (e.g., a patient table/bed/chair and a support platform).

An aspect of the invention pertains to a patient head protection device for protecting an upper body portion of a patient from collision with X-ray equipment, the device comprising:
a head protection shield comprising a face protector shield;
a support platform comprising a base unit for receiving a patient head;
a hinge for pivotably attaching the head protection shield to the support platform; and
an adjuster unit allowing to vertically adjust the distance between the face protector shield and the base unit, thereby allowing to fit various head sizes.

An aspect of the invention pertains to a patient head protection device for protecting an upper body portion of a patient from collision with moving parts of X-ray equipment, the device comprising:
a head protection shield comprising a face protector shield;
a vertical rear or side wall;
a hinge for pivotably attaching the head protection shield to the vertical rear or side wall;
attachment means to allow coupling the head protection device to a patient head platform; and
an adjuster unit allowing to vertically adjust the distance between the face protector shield and the patient head platform, thereby allowing to fit various head sizes.

In one or more embodiments, the adjuster unit is configured to adjust the distance of the shield from the patient's head platform or from a patient support platform to fit various head sizes and allow free head movements.

In some embodiments, the device includes attachment means to allow an attachment of the shield and/or a rear/side vertical wall thereof, and/or support platform to a subsystem and/or an add-on system, and/or a patient's head platform (e.g., patient table/bed/chair).

In some embodiments, the device includes attachment means to allow an attachment of the shield and/or a vertical wall thereof to a patient's head platform.

In some embodiments, the patient's head platform selected from a patient table, a patient bed, and a patient chair.

In one or more embodiments, the attachment means allow a permanent fixature. In one or more embodiments, the attachment means allow a temporary fixature.

In one or more embodiments, the support platform is configured to support a patient's head.

In one or more embodiments, the support platform is configured to attach a patient's bed/table.

In one or more embodiments, the support platform is affixed to a patient's bed/table.

In one or more embodiments, the support platform is integrally attached to a patient's bed/table.

In one or more embodiments, the head protection shield includes a top face protector shield for shielding a patient's face.

In one or more embodiments, the head protection shield includes a top face protector shield for shielding a patient's face and side protector shields extending downwardly from the face protector shield and configured to protect the sides of the patient head.

In one or more embodiments, the head protection shield includes an elongated rod extending from the face protector shield.

In one or more embodiments, the support platform is having a base unit for receiving head of the patient, a rear unit extending vertically from the base unit covering the back side of the head and an attachment unit in the form of a hinge which allows pivot movement of the head protector shield with respect to the support platform.

In one or more embodiments, the head protection device is manufactured from a radiolucent material.

In one or more embodiments, the head protection device is manufactured from rigid composite material. In one or more embodiments, the head protection device is manufactured from carbon fibers.

Another aspect of the present invention is to provide an adjuster unit configured to allow vertical movement of the support platform and the head protection shield relative to each other. In one or more embodiments, the adjuster unit allows movement of the head protection shield with respect to the support platform.

In one or more embodiments, the adjuster unit includes a sliding mechanism allowing a vertical sliding motions between the support platform and the head protection shield. In one or more embodiments, the adjuster unit comprising a sliding mechanism, allowing the vertical movement of the face protector shield with respect to the base unit. In one or more embodiments, the adjuster unit is motorized allowing a motorized vertical motion. In one or more embodiments, the adjuster unit includes a telescopic structure which can extend and retract, scissors lifting mechanism, a lever, a hydraulic lift.

In one or more embodiments, the adjuster unit includes an elongated rod which can slide or vertically move within dedicated hollow brackets, wherein the elongated rod attached to the head protection shield and the brackets attached to the support platform or vice versa.

In one or more embodiments, the adjuster unit comprises a hollow bracket having an opened top end and a bottom end; wherein the head protection shield comprises an elongated rod extending from the face protector shield and wherein the hollow bracket configured to receive the elongated rod via the open top end and to allow a vertical movement of the elongated rod within the hollow bracket.

In one or more embodiments, a sliding mechanism includes a rail and a sliding element, wherein the rail attached to the head protection shield and the sliding element attached to the support platform, or vice versa.

In one or more embodiments, the support platform includes a vertical wall extending perpendicular from the base unit.

In one or more embodiments, the vertical wall having a groove on the rear surface thereof and configured to receive the adjuster unit. In one or more embodiments, the support platform includes a rear wall having a groove on the rear surface thereof and configured to receive the adjuster unit. In one or more embodiments, the support platform includes a side wall having a groove on the rear surface thereof and configured to receive the adjuster unit.

In one or more embodiments, the support platform includes a vertical wall extending perpendicular from the base unit, wherein the hinge connects the head protection shield to the support platform via a rear surface of the vertical wall.

In one or more embodiments, the adjuster unit includes a hollow bracket configured to fit in the groove and receive a sliding element (e.g., an elongated rod) of the head protection shield. In one or more embodiments, a hinge attaches the head protection shield to the support platform to allow the pivotal movement between the head protection shield and the support platform.

In one or more embodiments, the hinge connecting the shield to the support platform allows a rotational/pivotal movement of the shield relative to the support platform, allowing closing and opening the shield and positioning a patient's head inside the head protection device.

In one or more embodiments, a pivotal movement include up to about 90° movement of the shield relative to the support platform.

In one or more embodiments, the support platform comprises a rear wall extending vertically from the base unit, wherein the rear wall manufactured from a radiation attenuating material for protecting medical personnel from scattered radiation in areas behind the patient's head. In one or more embodiments, the support platform comprises a side wall extending vertically from the base unit, wherein the side wall manufactured from a radiation attenuating material for protecting medical personnel from scattered radiation in areas behind the patient's head.

In one or more embodiments, the rear/side wall manufactured from a layered composite material comprising one or more layers of a radiation attenuating material and one or more layers of carbon fiber. In one or more embodiments, the composite material comprising: one or more carbon fiber layers; a binding material; and a radiation attenuating material applied onto and/or between the one or more carbon fiber layers. In one or more embodiments, the binding material is applied onto and/or between the one or more layers of carbon fibers and configured to at least partially adhere thereto; and the radiation attenuating material applied onto and/or between the one or more carbon fiber layers. In one or more embodiments, the binding material is a polymer. In one or more embodiments, the binding material is selected from a thermoset resin, polyester, vinyl ester, nylon, and a combination thereof. In one or more embodiments, the thermoset resin is epoxy resin.

In one or more embodiments, the rear/side wall manufactured from a non-layered composite material comprising a mixture of one or more polymers and one or more radiation attenuating material(s). In one or more embodiments, the radiation attenuating material(s) is provided as a powder which is substantially homogenously dispersed in the one or more polymers. In one or more embodiments, the polymer is a thermoplastic material (e.g., a polyamide).

In one or more embodiments, the radiation attenuating material is a metal selected from selected from a group consisting of tungsten, lead, bismuth, antimony, barium, tantalum, and a combination thereof.

Another object of the present invention is to provide a stopper for locking the shield to the support platform and thereby locking the pivotal movement of shield with respect to the support platform.

In one or more embodiments, the adjuster unit comprises a locking member configured to adjust the distance of the shield from the support platform/patient head platform and lock the vertical movement of the shield with respect to the platform.

In one or more embodiments, the adjuster unit comprises a knob configured to lock the vertical movement of the shield with respect to the support platform/patient head platform.

In one or more embodiments, the shield is manufactured from a radiolucent material and carbon fibers.

In one or more embodiments, the support platform is manufactured from a radiolucent material and carbon fibers.

In one or more embodiments, the head protection device further comprising fixature means for connecting the head protection device to a patient's table/bed/chair.

In one or more embodiments, the head protection device is devoid of any electronic means. In one or more embodiments, the head protection device is devoid of any electronic coils.

In one or more embodiments, the head protection device comprising one or more openings to allow comfort, relaxing and/or airy environment for the user.

In one or more embodiments, one or more openings are configured in the shield.

In one or more embodiments, the device includes a speaker to generate audio signals. In one or more embodiments, the device includes a microphone to receive audio signals. In one or more embodiments, the device includes a camera to capture visuals. In one or more embodiments, the device includes a display unit to display visuals. In one or more embodiments, the device includes a bi-directional communication unit to communicate the visual and/or audio signals over a communication network.

In one or more embodiments, the device includes a battery to power the bi-directional communication unit, the display unit, the camera, the microphone and/or the speaker.

In one or more embodiments, the head protection device is configured to create a physical barrier between a patient's head and an imaging system and/or an imaging add-on system (e.g., a radiation shielding apparatus) or a part thereof.

In one or more embodiments, the head protection device is made of a material visible to a sensor (e.g., carbon fiber, thermoplastic resins, gel-based water).

In one or more embodiments, the head protection device is made of a material visible to a collision sensor.

In one or more embodiments, the head protection device is made of a material visible to a proximity or contact sensor.

In one or more embodiments, the device includes a collision sensor configured in the shield to detect collisions.

In one or more embodiments, the sensor is selected from a capacitive sensor, a resistive sensor, a capacitive-resistive sensor, an ultrasonic sensor, an electro-optic sensor, a contact sensor, a strain sensor, a temperature sensor (thermocouple), and a combination thereof.

In one or more embodiments, the head protection device is permanently connected to the patient's table or to an operation table. In one or more embodiments, the head protection device is temporarily connected to the patient's table or to an operation table.

In one or more embodiments, the head protection device is provided as a stand-alone apparatus.

In one or more embodiments, the head protection device includes attachment means to allow connecting the head protection device to a sub-system and/or an add-on system.

In one or more embodiments, the head protection device is integrally attached to a sub-system and/or an add-on system.

In one or more embodiments, the sub-system and/or an add-on system is selected from an X-ray system or a portion thereof (e.g., a C-arm), a radiation shielding apparatus or a portion thereof, and a combination thereof.

In one or more embodiments, the head protection device is equipped with a speaker, a microphone, a camera, a display screen or a combination thereof.

In one or more embodiments, the shield or portion thereof is at least partially transparent or translucent.

An aspect of the invention pertains to an X-ray equipment comprising:
an X-ray radiation shielding apparatus comprising:
an X-ray radiation shield positioned around an X-ray source of a movable X-ray robotic arm; and
an X-ray radiation shield positioned around an X-ray detector of a movable X-ray robotic arm; and
a patient head protection device comprising:
a head protector shield;
a support platform comprising a base unit for receiving a patient head;
a hinge for pivotably attaching the head protection shield to the support platform; and
an adjuster unit allowing to vertically adjust the distance between the face protector shield and the base unit, thereby allowing to fit various head sizes.

An aspect of the invention pertains to an X-ray equipment comprising:
an X-ray radiation shielding apparatus comprising:
an X-ray radiation shield positioned around an X-ray source of a movable X-ray robotic arm; and
an X-ray radiation shield positioned around an X-ray detector of a movable X-ray robotic arm; and
a patient head protection device comprising:
a head protector shield;
a vertical rear or side wall;
a hinge for pivotably attaching the head protection shield to the vertical or side wall; and
attachment means to allow coupling the head protection device to a patient head platform; and
an adjuster unit allowing to vertically adjust the distance between the face protector shield and the patient head platform, thereby allowing to fit various head sizes.

In one or more embodiments, the movable robotic arm is a C-arm device.

In one or more embodiments, the radiation shielding apparatus includes moveable X-ray radiation source shield and X-ray detector radiation shield. In one or more embodiments, the X-ray radiation source shield and X-ray detector radiation shield are contractable and extendable. In one or more embodiments, the X-ray radiation source shield and X-ray detector radiation shield include a plurality of contractable, and extendable segments positioned sequentially adjacent to each other, forming a contiguous radiation shielding.

An aspect of the invention provides a method of protecting a head of a patient during an X-ray medical procedure, the method comprising:
providing a head protection device comprising a head protection shield;
opening the device by a pivotal movement of the shield with respect to a patient head platform;
positioning a patient's head on the patient head platform;
closing the head protection device;
adjusting a height of the head protection shield with respect to the patient head platform using an adjuster unit of the head protection device; and
performing the medical procedure.

In one or more embodiments, closing the head protection device is via a pivotal movement of the shield with respect to the patient head platform.

In one or more embodiments, adjusting a height of the head protection shield with respect to the patient head platform includes vertically moving the shield downwardly or upwardly.

In one or more embodiments, the method comprising locking the pivotal movement via a stopper disposed on a wall of the head protection device.

In one or more embodiments, the method further comprising locking the vertical movement via a knob in the adjuster unit.

In one or more embodiments, then method further comprising locking the vertical movement via a locking member in the adjuster unit.

In one or more embodiments, the patient head platform selected from a patient table, a patient chair, a patient bed and a support platform pivotally connected to the head protection shield.

In one or more embodiments, the method further comprises attaching the head protection device to the patient head platform, to a sub-systems or to an add-on system.

Unless otherwise defined, all technical or/and scientific terms used herein have the same meaning as commonly understood by one of ordinary skill in the art to which the invention pertains. Although methods and components/materials similar or equivalent to those described herein be used in the practice or testing of embodiments of the invention, exemplary methods or/and components/materials are described below. In case of conflict, the patent specification, including definitions, will control. In addition, the materials, components, methods, and examples are illustrative only and are not intended to be necessarily limiting.

BRIEF DESCRIPTION OF DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 1:
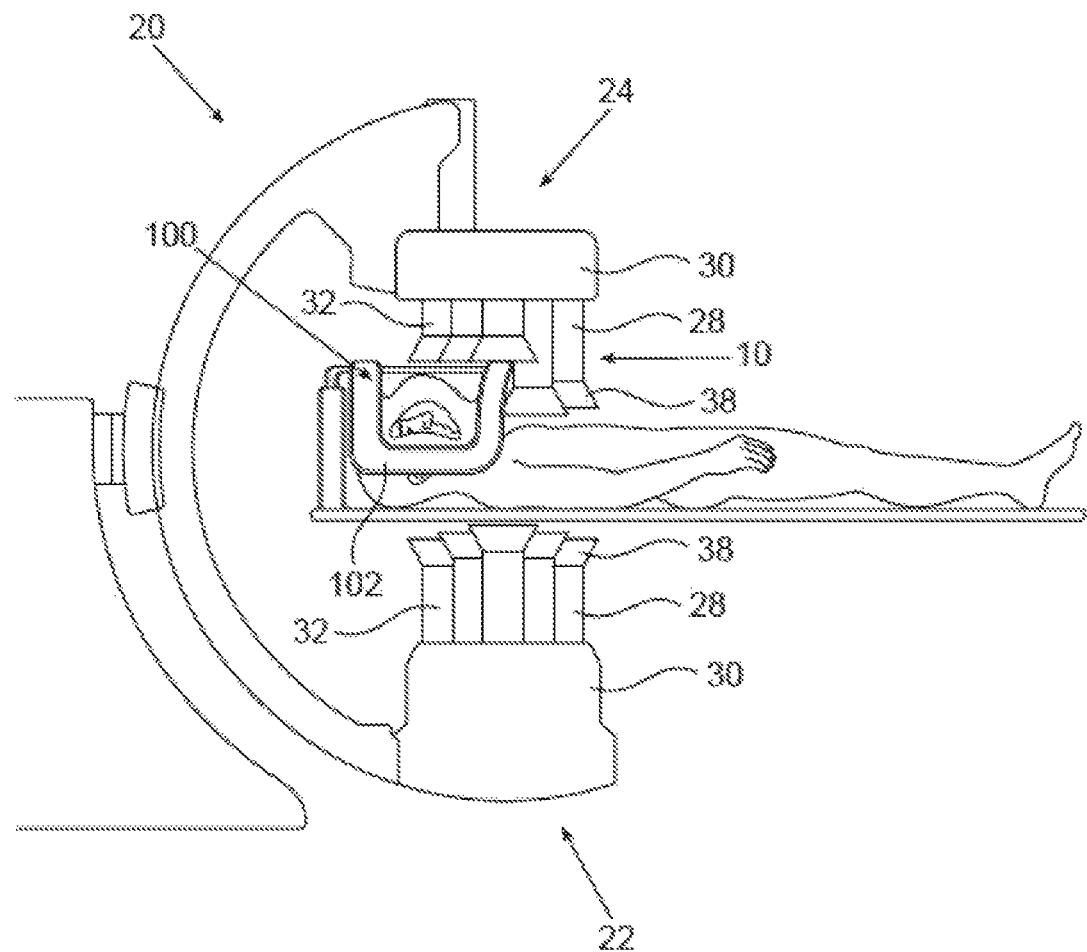
FIG. 1 is a side view of a radiation protection apparatus and a head protection device, according to embodiments of the present invention.

It should be appreciated that for simplicity and clarity of illustration, elements shown in the figures have not necessarily been drawn to scale. For example, the dimensions of some of the elements are exaggerated relative to each other for clarity. Further, where considered appropriate, reference numerals have been repeated among the figures to indicate corresponding elements.

DETAILED DESCRIPTION OF THE INVENTION

It is understood that the invention is not limited to the particular methodology, devices, items or products etc., described herein, as these may vary as the skilled artisan will recognize. It is also to be understood that the terminology used herein is used for the purpose of describing particular embodiments only and is not intended to limit the scope of the invention. The following exemplary embodiments may be described in the context of exemplary head protection devices for ease of description and understanding. However, the invention is not limited to the specifically described products and methods and may be adapted to various applications without departing from the overall scope of the invention. All ranges disclosed herein include the endpoints.

The use of the term "or" shall be construed to mean "and/or" unless the specific context indicates otherwise.

Special care should be taken concerning possible collisions of angiography and/or fluoroscopy systems (e.g. Full-sized fixed C-arm and mobile C-arm) with a patient's sensitive areas like head, face and neck.

The current invention, in some embodiments thereof, relates to a dedicated patient head protection device. The device creates a physical barrier between the patient's head and face and optionally neck and potentially harmful objects. For example, for a fluoroscopic X-ray system, the head protection device may protect the patient's face from moving parts of the C-arm that might collide with it. In some embodiments, the device is intended to provide full protection for areas of head, face and neck of the patient.

The head protection device of the invention may confer one or more of the following attributes:
1. the head protection device is made of a material (e.g. carbon fiber) that provides strong and rigid protection; and/or
2. the head protection device is made of a material visible to a collision sensor (for example carbon fiber is visible to a capacitive technology collision detector that may be used on an imaging device); and/or
3. the head protection device is made of a material that does not interfere with the equipment in use. For example, a head protection shield may be radiolucent to radiation in a certain band to facilitate imaging using radiation in that band (for example carbon fiber is radiolucent to radiation of some imaging devices for example X-rays); and/or
4. the head protection device includes one or more openings to allow an airy environment to a user; and/or
5. the head protection device is configured to adjust various head sizes or can be adjusted to allow varying degrees of space to a user.

In an aspect of the invention, the head protection device includes a support platform for supporting a patient's head; and a head protection shield connected to the support platform and enclosing a space for accommodating a patient's head.

The head protection device may be at least partially transparent or translucent, allowing the medical staff to visualize the patient and vice versa.

The head protection device may include broadcasting and/or communication means to allow communication between the patient and the medical staff. Non-limited examples of broadcasting and/or communication means include a speaker, a microphone, a camera (e.g., a video camera), a display screen or a combination thereof.

The distance of the shield from the support platform of the head protection device can be conveniently adjusted to fit to various head sizes and shapes.

Further advantageously, an attachment unit, e.g., a hinge connecting the shield to the support platform allows convenient opening and closing of the device, optionally via a one dimensional rotation or partial rotation movement.

Yet further advantageously, the head protection device of the invention may optionally include attachment or fixature means to allow an attachment to a sub-system and/or an add-on system. Exemplary sub-systems include, without limitation, an X-ray system or a portion thereof (e.g., a C-arm). Exemplary add-on systems include, without limitation, radiation shielding apparatuses, the teachings of which are provided in the following disclosures: U.S. Pat. Nos. 8,439,564, and 8,113,713, US patent application No. 2018/0168525, International patent application No. WO 2017/083437, and US patent application No.: 2018/0249972, the content of which are incorporated by reference as if fully set forth herein.

The head protection device may be made of a material visible to a collision sensor. Non-limited examples of collision sensors include, a capacitive sensor, a resistive sensor, a capacitive-resistive sensor, an ultrasonic sensor, an electro-optic sensor, a contact sensor, a strain sensor, and a combination thereof.

Non limited examples of materials visible to a collision sensor include carbon fiber and water, or water-based gel which may be implemented herein within dedicated tubes.

The head protection device includes an adjuster unit for allowing vertical movements of a head protection shield and adjusting the distance of the shield with respect to a patient bed/table/chair. Various adjuster mechanisms are contemplated as long as those mechanisms afford the vertical movement of the shield. Exemplary mechanisms include sliding mechanisms wherein at least two elements slide with respect to each other and allow an extension of at least one of the elements. The sliding mechanism may include a rail and a sliding element. Additional exemplary mechanisms include telescopic structures which can extend and retract, scissors lifting mechanism (e.g., scissors lifting jack), a lever, a hydraulic lift mechanism and any of the alike vertical lifting elements/means. The above adjuster mechanisms may be motorized, for example, via an electrical motor, a pneumatic motor, a hydraulic motor.

FIG. 1 schematically illustrates an exemplary C-arm 20 of an X-ray system and an exemplary radiation shielding apparatus 10 which intends to limit/reduce exposure to radiation of personnel and technicians who work with and near X-ray radiation systems, such as C-arm 20. FIG. 1 further illustrates an exemplary head protection apparatus 100 which creates a physical barrier between the patient's head and optionally neck and potentially harmful moving parts of the C-arm 20 and/or radiation shielding apparatus 10. The apparatus 10 is shown in conjunction with a typical C-arm 20 of an X-ray system for performing an X-ray image of a patient. The X-ray system includes a radiation source 22 and a radiation detector 24 mounted on opposing ends of C-arm 20. The apparatus includes a radiopaque or radiation attenuating/blocking shield, which includes at least one radiation shield assembly 28 (e.g. above and below the patient, as illustrated) having a support base 30 operatively connectable to radiation source 22 and/or operatively connected to radiation detector 24, which are mounted on opposite ends of C-arm 20.

Radiation shield assembly 28 may optionally include a plurality of radiation shield segments 32 sequentially positioned relative to support base 30, thereby forming radiopaque screen radiation attenuating/blocking shield in a contiguous configuration.

Shield assembly 28 has free edge ends 38 for spanning the periphery of a body region of the patient. Radiation shield segments 32 are controllable to extend or contract to a selected length to position respective free ends 38 in proximity of the patient, or an object such as an X-ray table.

A head protection device 100 is further provided to protect a patient head and provide collision protection from moving parts of C-arm 20 and/or radiation shielding apparatus 100. As will be illustrated in greater detail below, the head protection device 100 includes a head protection shield 102 essentially made of a rigid material which is adjustable in terms of height/distance of the shield with respect to a patient head platform, or support platform (e.g., support platform 104 shown in FIGS. 2-12).

Figures 2, 3:
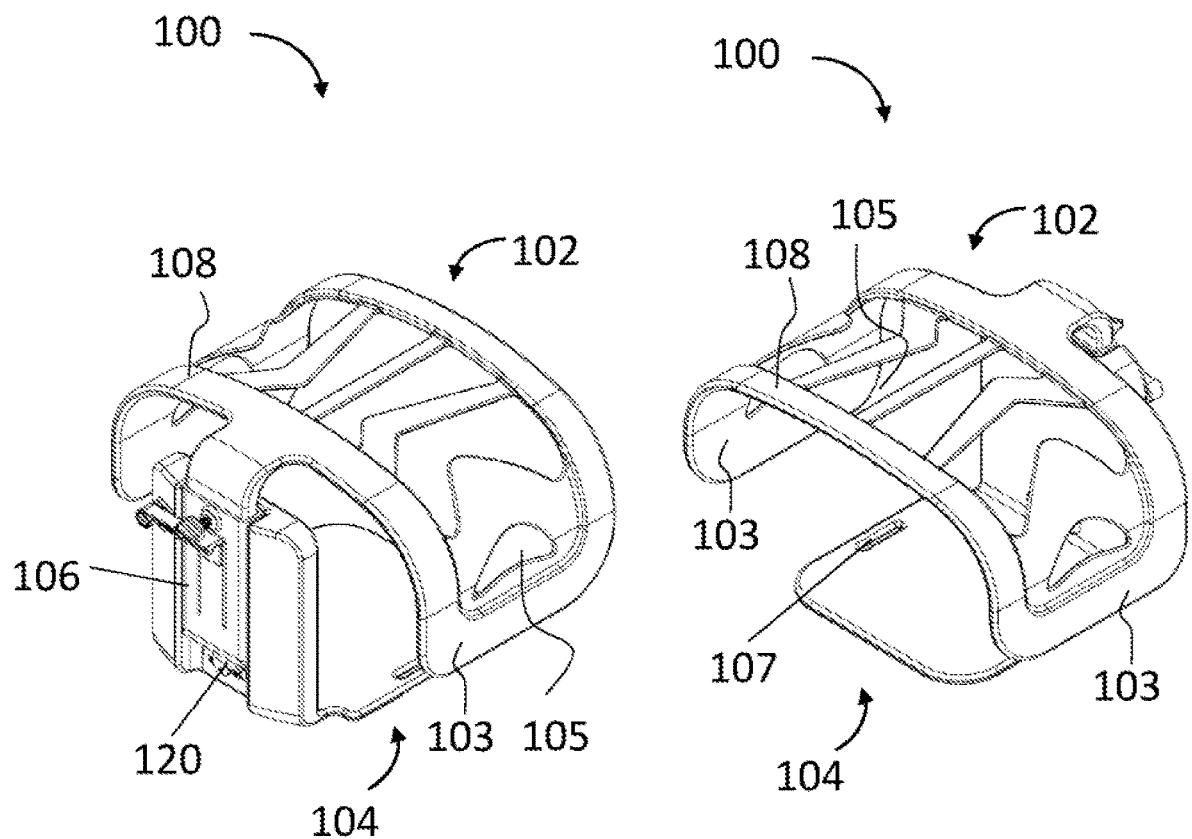
FIG. 2 illustrates a rear perspective view of an exemplary head protection device, according to some embodiments of the invention.
FIG. 3 illustrates a front perspective view of the device of FIG. 2, according to some embodiments of the invention.

FIGS. 2 and 3 illustrate an exemplary head protection device 100 in accordance with embodiments of the current invention. FIG. 2 illustrates a rear perspective view of the device 100. FIG. 3 illustrates a front perspective view of the device 100. The device 100 includes a head protection shield 102, attached to a support platform 104 via a hinge 120. Head protection shield 102 includes a top face protection shield 108 and opposing side protection shields 103 extending downwardly from the top face protection shield 108. The device 100 further includes an adjuster unit 106 for adjusting a distance between face protection shield 108 of shield 102 and support platform 104. In some embodiments, the face/head protection shield (e.g. a mask) 108 has two degrees of freedom, i.e., vertical, via adjuster unit 106, and/or rotational/pivotal, via hinge 120. Optionally, but not necessarily the face/head protection shield (e.g. a mask) 108 has no more than two degrees of freedom. Vertical movement includes, for example, moving shield 102 towards and away from support platform 104 to enable close fit for different head sizes and/or to facilitate maneuvering by a lab staff and equipment. Rotational movement includes, for example, rotation around a fulcrum (hinge 120) at the bottom of the device near the support platform 104 to enable head positioning. Optionally, all mechanisms are radiolucent and/or non-radiolucent parts (like a hinge) are located behind the patient, and/or on the sides of the patient, and/or between the patient and the support and/or next to the support. The face/head protection shield 102 optionally has one or more openings 105 to ensure comfort, relaxing and/or airy environment for the patient.

The device 100 optionally has features (i.e., attachment means) enabling fixture and/or release and/or movement relative to a patient table, for example, the support platform 104 may include slots 107 suitable for standard straps, for example, to strap the support platform 104 to a table and/or loosen the support platform 104 from the table for moving and/or to remove the device 100 from the table.

Figure 4:
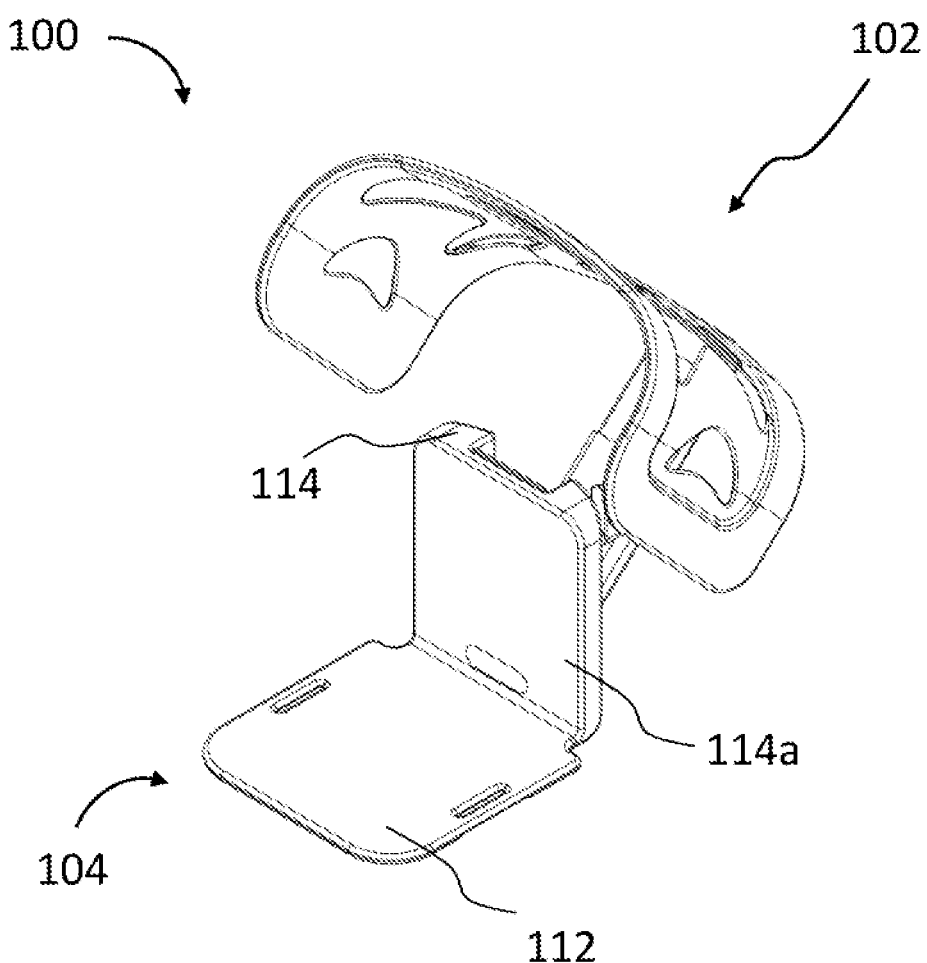
FIG. 4 illustrates a perspective view of the device of FIG. 2 when in an open position, according to some embodiments of the invention.

In FIG. 4 device 100 is shown when shield 102 in an open position. The support platform 104 includes a base unit 112 and a vertical rear wall 114 extending perpendicular from the support platform 104 and having a front surface 114*a*. The shield 102 when in an open position allows a patient to place his head on the base unit 112. Optionally, rear wall 114 is manufactured from a radiation blocking/attenuating material to thereby protect the medical staff from scattered radiation in areas behind the patient's head. For example, the rear wall 114 may be manufactured from a radiation attenuating material, such as a radiation attenuating metal (e.g., tungsten, lead, bismuth, antimony, barium, tantalum, and a combination thereof). To allow rigidity, the rear wall may be manufactured from a composite material comprising a radiation attenuating metal (optionally in the form of a foil or a powder). Optionally, the rear wall may be manufactured from a composite material comprising carbon fiber and a radiation attenuating metal (optionally in the form of a foil). The composite material may be in the form of layers of one or more carbon fibers and one or more layers of a radiation attenuating material. Optionally, the composite material may include a binding material (e.g., a thermoset resin) such to act as an adhesive between the layers and contribute to the rigidity and strength of a structure when combined with the fibers. Optionally, the composite material includes a radiation attenuating material in the form of a powder mixed within a binding material, and wherein such mixture is applied onto at least one of the fibers. Further optionally, the composite material includes a thermoplastic material mixed with a radiation attenuating material.

Figure 5:
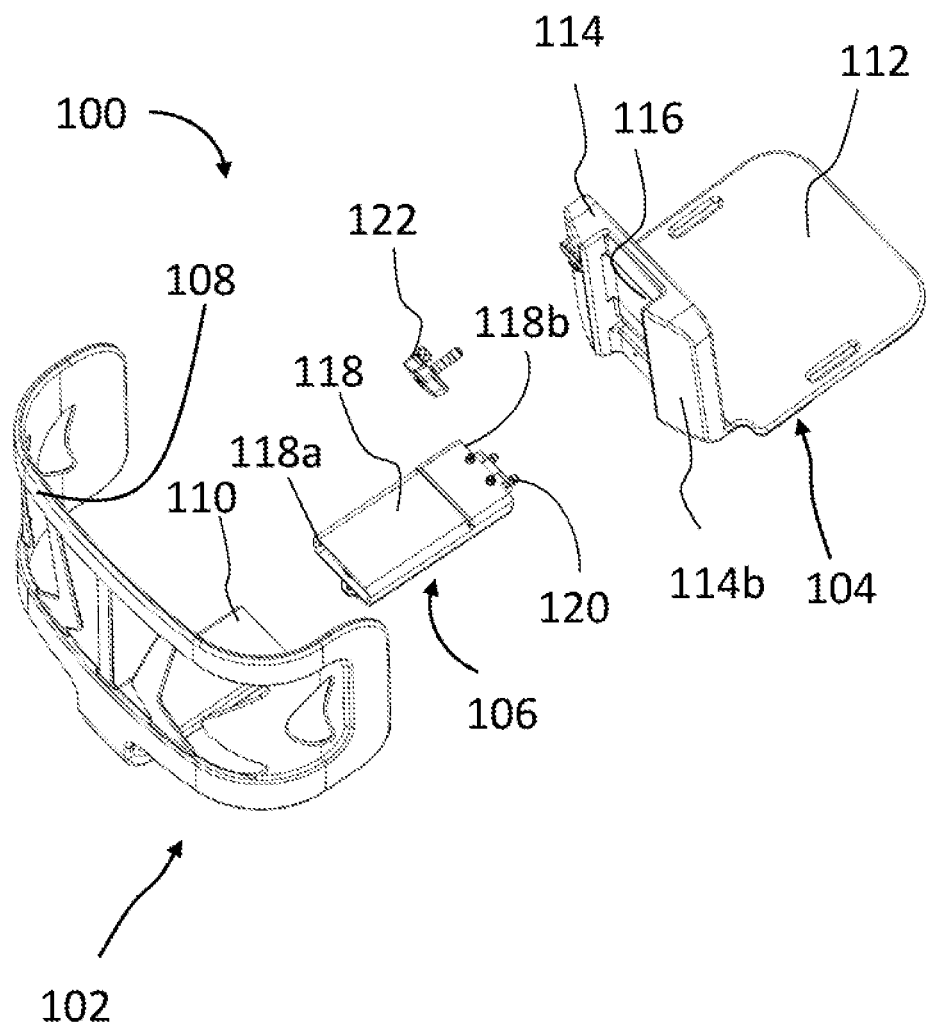
FIG. 5 illustrates a perspective exploded view of the device of FIG. 2, according to some embodiments of the invention.

FIG. 5 illustrates a perspective exploded view of device 100. The shield 102 includes a face protector shield 108 for protecting face of the user, and an elongated rod 110 extending from the face protector shield 108. The support platform 104 is pivotably attached to shield 102 via hinge 120. The support platform 104 includes a base unit 112, a rear wall 114 and a groove 116. The base unit 112 is configured to receive a head of the user. The rear wall 114 is extending vertically from the base unit 112. The rear wall 114 is having a front surface (114*a*, shown in FIG. 4) and a rear surface 114*b*. The rear wall 114 covers the top of the head of a patient. The groove 116 is configured on the rear surface 114*b*. An adjuster unit 106 is configured to allow for a vertical movement of face protector shield 108 with respect to base unit 112, thereby allowing to adjust the distance between face protector shield 108 and base unit 112. Various mechanisms of an adjuster unit are contemplated and may include, for example, a sliding element which is slidable within a rail or a bracket 118 as will be described herein below in greater details. The adjuster unit 106 pivotally attaches via hinge 120 the support platform 104 to the shield 102. The adjuster unit 106 includes a hollow bracket 118 configured to allow sliding therein of a sliding element, herein elongated rod 110, optionally up to full evacuation of rod 110 and the full release of shield 102. The hollow bracket 118 is configured to fit in the groove 116. The hollow bracket 118 is having an open top end 118*a* and a bottom end 118*b*. The open top end 118*a* receives the elongated rod 110.

The hinge 120 attaches to the bottom end 118*b* to facilitate pivot movement of the shield 102 with respect to the support platform 104. Nevertheless, alternative locations of the hinge are contemplated, such as an attachment of hinge 120 to a middle location or a higher location in rear surface 114*b*. Pivotal movement includes, up to about 90° opening of shield 102 with respect to support platform 104. For example, 45° opening of shield 102 with respect to support platform 104 (shown for example in FIG. 7). The pivotal movement may include, for example, 90° opening of shield 102 with respect to support platform 104 (shown for example in FIG. 11). A threaded knob 122 can extend through the bracket 118 and configured to lock the vertical movement of shield 102 with respect to support platform 104.

Figure 6:
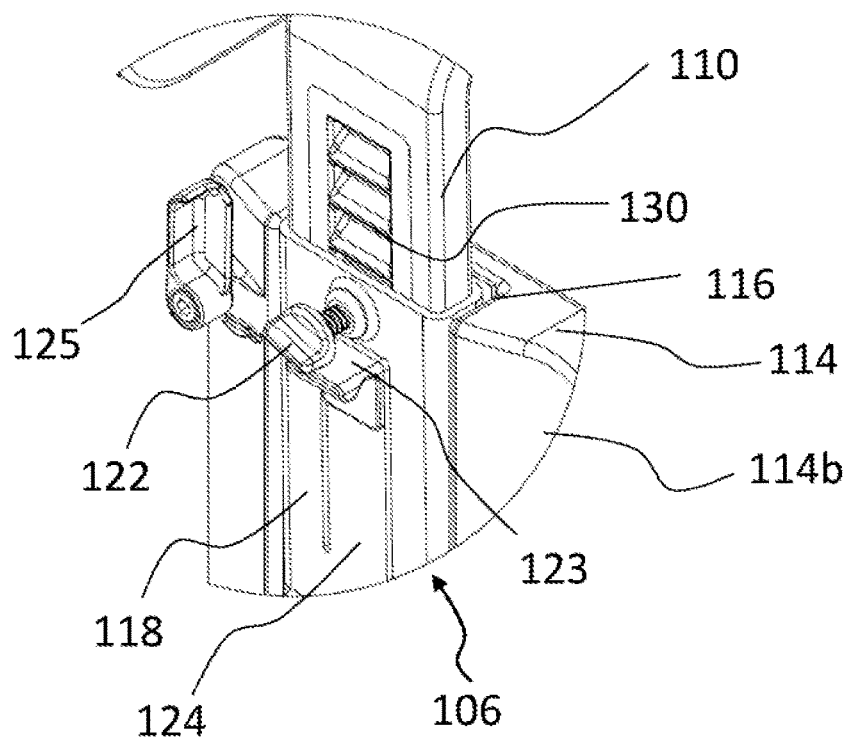
FIG. 6 illustrates a magnified perspective view of a portion of a rear wall, and an adjuster unit of a device, according to some embodiments of the invention.

FIG. 6 illustrates a rear perspective view of the rear surface 114*b* of rear wall 114, the elongated rod 110 and the adjuster unit 106. The groove 116 configured on the rear wall 114 to receive the hollow bracket 118. The shape of the groove 116 may geometry fit the shape of the hollow bracket 118. A locking member 123 is configured within bracket 118 and locks the vertical movement of the elongated rod 110 inside the hollow bracket 118. The elongated rod 110 further includes one or more grooves/slots 130 to receive an internal tab-like portion (not shown) of locking member 123 and thereby lock the vertical movement of the shield. Locking member 123 is made of a resilient material allowing backward retraction thereof to thereby allow the movement of the elongated rod 110 within bracket 118 and adjust the distance of the shield 102 from the support platform 104 to fit various head sizes. When locking member 123 is released it is capable of locking the vertical movement and fixate the height of the elongated rod 110 inside the hollow bracket 118.

A knob 122 is further disposed on rear surface 114*b* to further stop the vertical movement of the shield 102 with respect to support base 104. Stopper 125 is configured on rear wall 114b and locks the pivotal movement of shield 10 with respect to support platform 104 by an axial movement thereof.

Figure 7:
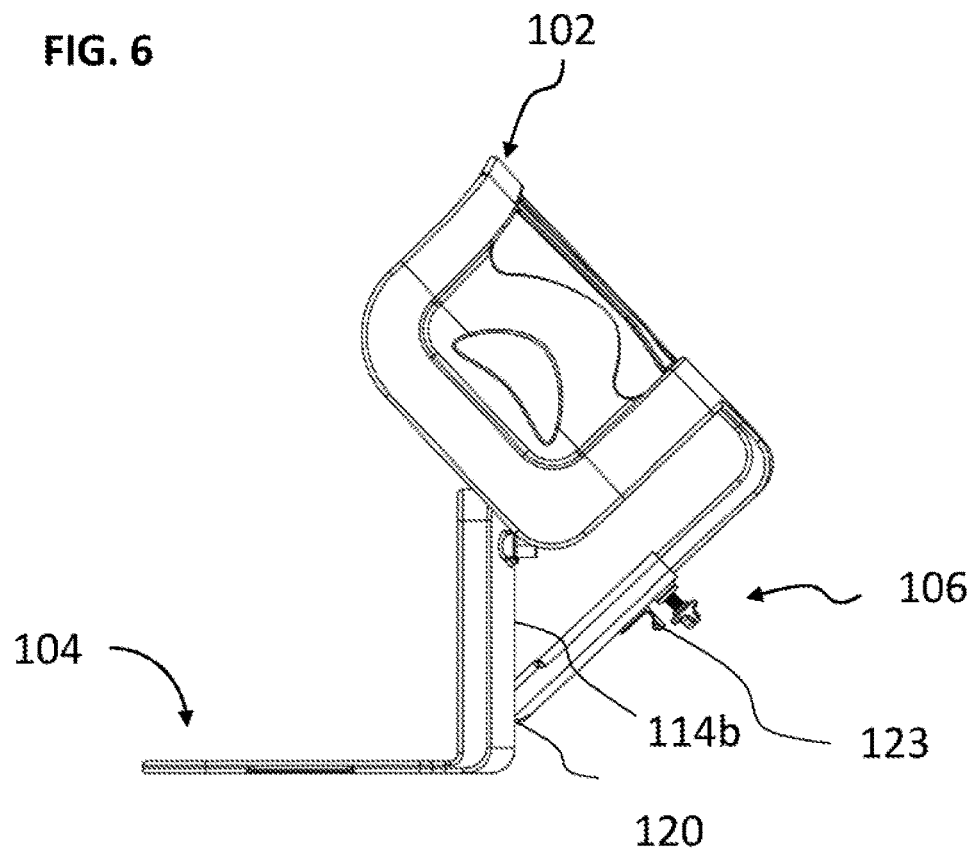
FIG. 7 illustrates a side view of the device of FIG. 2 when in an open position, according to some embodiments of the invention.

FIG. 7 illustrates a side view of device 100 when in an open position. A hinge 120 located at the bottom of rear wall 114 facilitates a pivotal movement, herein illustrated as about 45° and allows a patient to position its head on support platform 104. The adjuster unit 106 facilitates adjusting the height of the shield 102 with respect to support platform 104.

Figure 8:
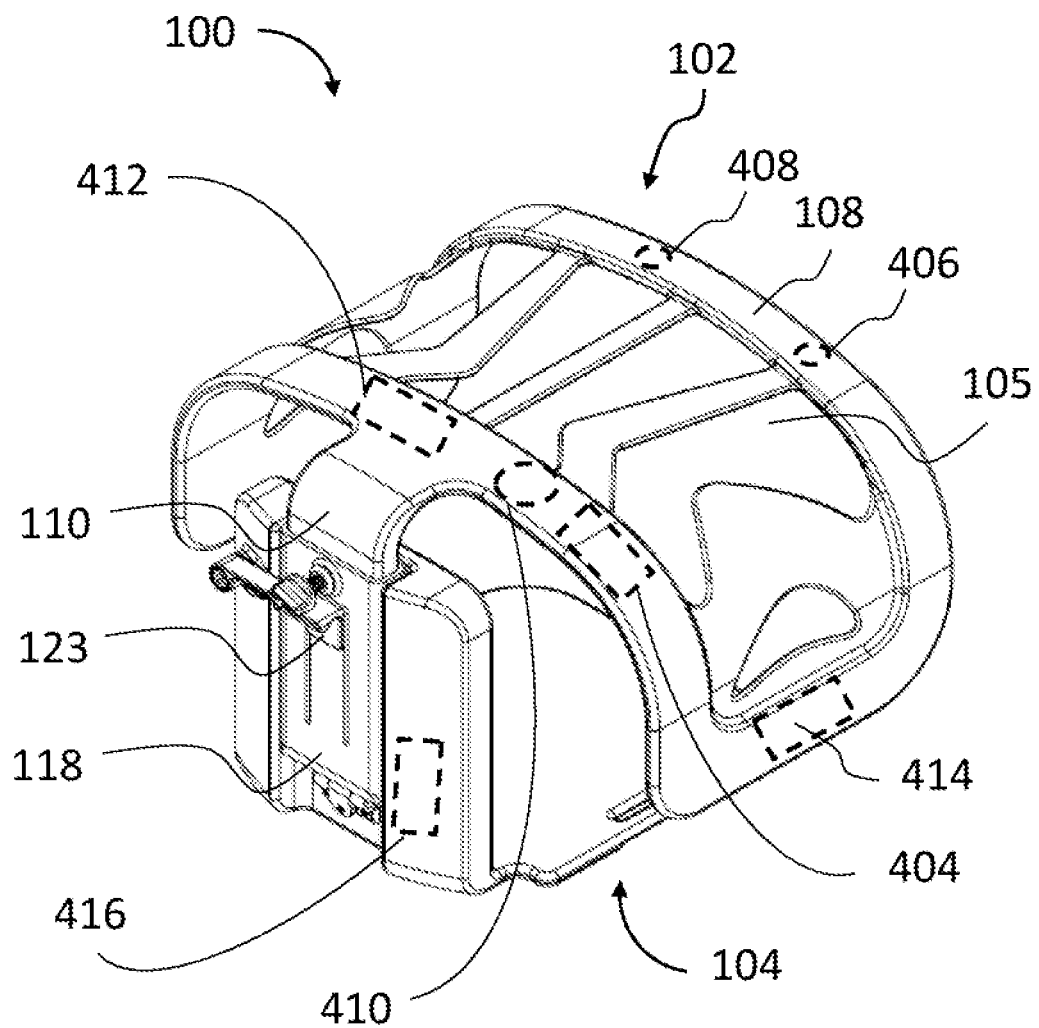
FIG. 8 illustrates a rear perspective view of the device of FIG. 2 when in a closed position, according to some embodiments of the invention.

FIG. 8 illustrates a rear perspective view of the device 100. The shield 102 is in closed position and the locking member 123 when manually retracted backwards allows the sliding of the elongated rod 110 within bracket 118 and when released locks the vertical movement of the elongated rod 110 inside the hollow bracket 118 to thereby adjust the distance of the shield 102 from the support platform 104 to fit various head sizes. The face protector shield 108 includes a plurality of openings 105 to allow comfort, relaxing and/or airy environment for the user. The openings 105 my form a grill-like pattern, a filter-like pattern or any alternative airy pattern, as long as the obtained products allows an airy environment to the patient.

The device 100 may include a collision sensor 404 configured in the shield 102 to detect collisions. Examples of collision sensor 404 include but not limited to a capacitive sensor, a resistive sensor, a capacitive-resistive sensor, an ultrasonic sensor, an electro-optic sensor, a contact sensor, a strain sensor, a temperature sensor (thermocouple), and a combination thereof.

The device 100 may further include one or more of a speaker 406 to generate audio signals, a microphone 408 to receive audio signals, a camera 410 to capture visuals, a display unit 412 to display visuals, a bi-directional communication unit 414 to communicate the visual and audio signals over a communication network, and a battery 416 to power the bi-directional communication unit 414, the display unit 412, the camera 410, the microphone 408 and/or the speaker 406. The speaker 406, microphone 408, camera 410, display unit 412, bi-directional communication unit 414, and/or battery 416 may be disposed on one or more positions in the protector shield 102 or on alternative locations, such as the support platform 104.

Examples of a communication network include but are not limited to Wi-Fi, Bluetooth, NFC, cellular etc. Examples a battery 416 include but not limited to a lithium ion battery, a lithium/silver vanadium oxide battery, a lithium polymer battery, rechargeable battery or a super-capacitor. Examples of a display unit 412 include but not limited to cathode ray tube (CRT) display, a liquid crystal display (LCD) or light emitting diode (LED) display etc.

Figures 9, 10:
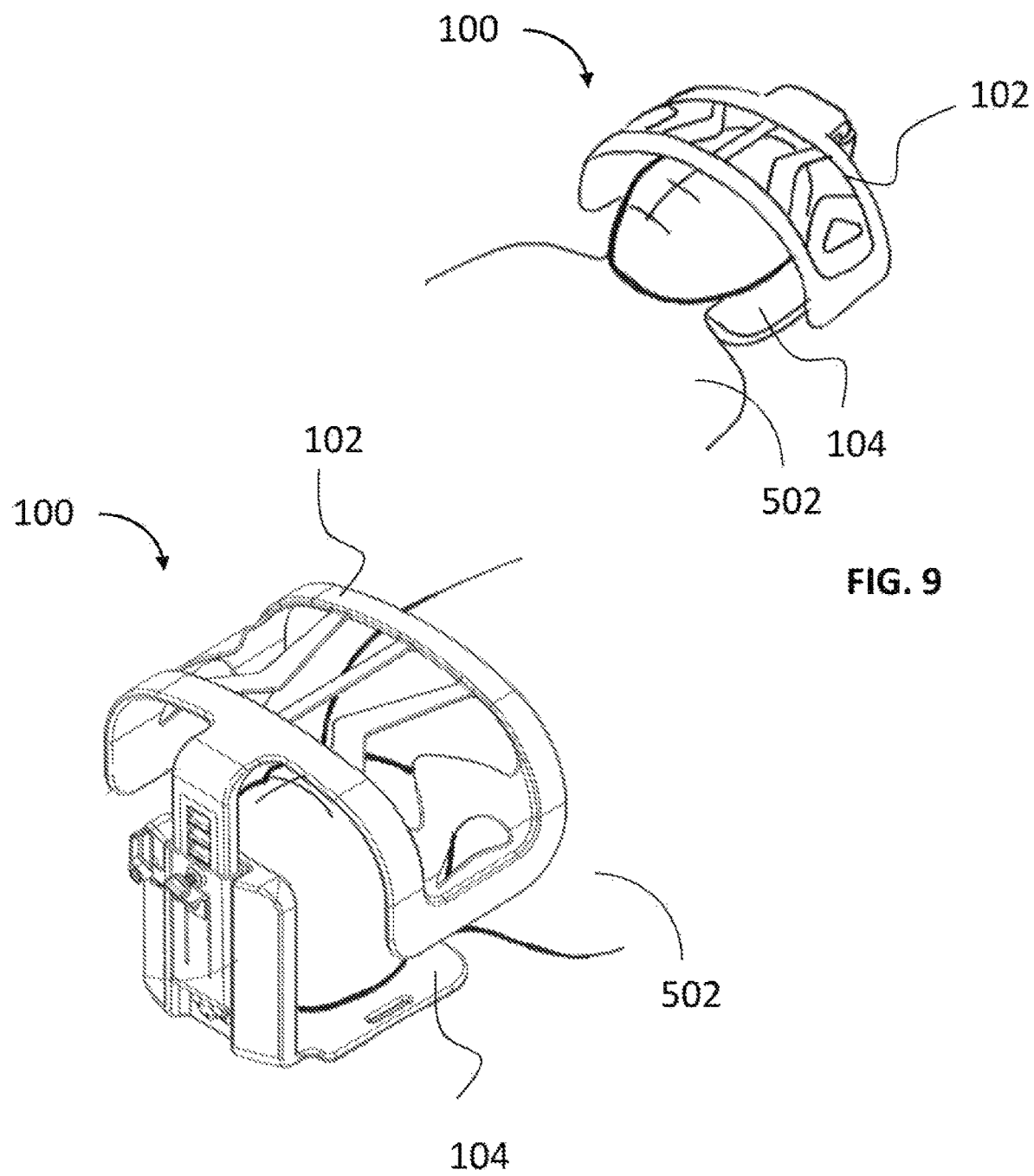
FIG. 9 illustrates a front perspective view of the device of FIG. 2 protecting a head of a user, according to some embodiments of the invention.
FIG. 10 illustrates a rear perspective view of the device of FIG. 2 protecting a head of a user, according to some embodiments of the invention.

FIGS. 9 and 10 illustrate a perspective front view (FIG. 9) and a perspective back view (FIG. 10) of the device 100 protecting upper body of a patient 502. The device 100 may be connected to bed, chair, table, X-ray systems etc. via attachment means (not shown) to connect the support platform 104 or shield 102 to the bed, chair, table, X-ray systems, and/or X-ray radiation shielding apparatus. The shield 102 covers the face of the user 502 and is shown in closed position.

Figure 11:
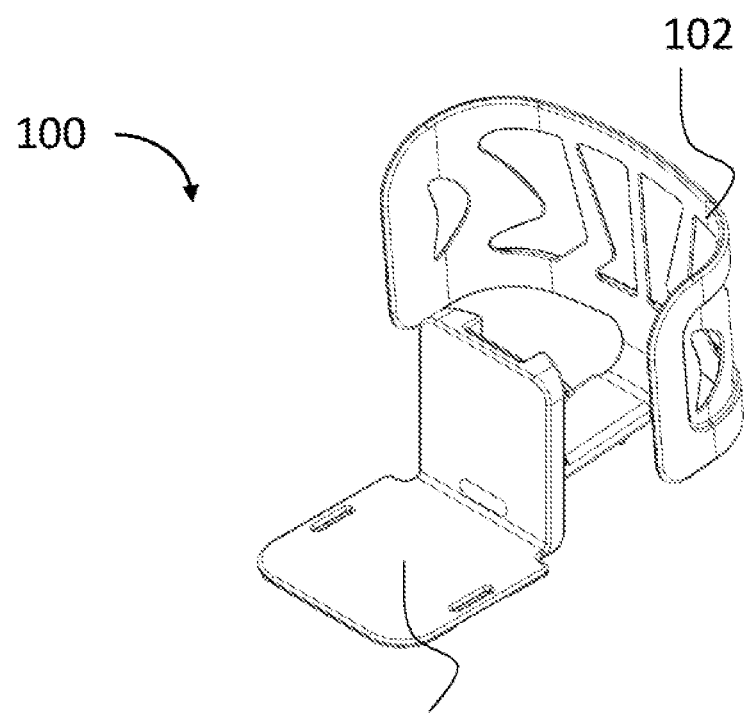
FIG. 11 illustrates the device of FIG. 2 when in an open position, according to some embodiments of the invention.

FIG. 11 illustrate the device 100 when the shield 102 fully opened, i.e., the pivotal movement includes, for example, 90° opening of shield 102 with respect to support platform 104.

Figure 12:
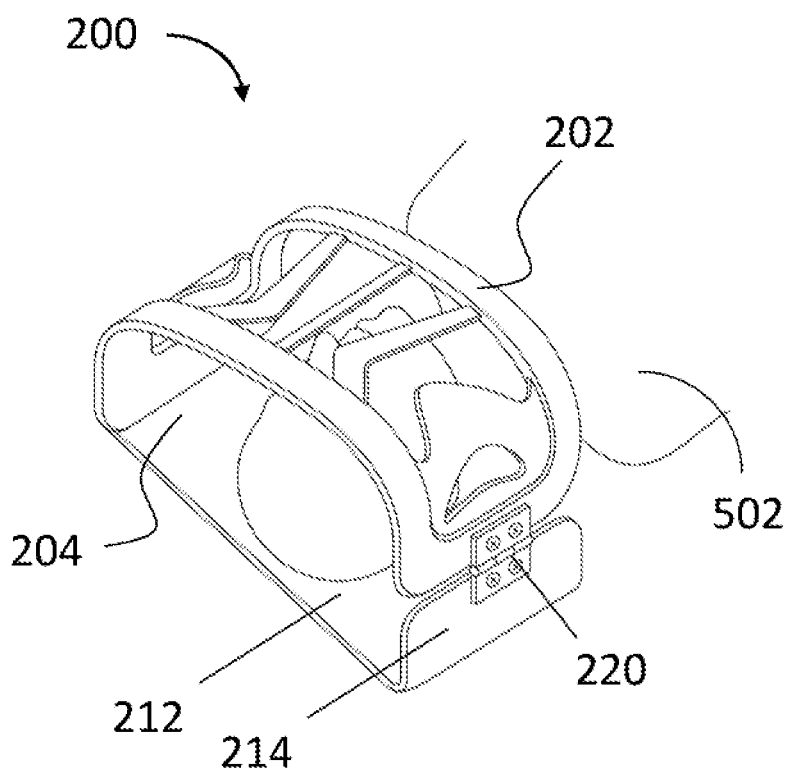
FIG. 12 illustrates an exemplary head protection device with a side opening pivotal movement mechanism, according to some embodiments of the invention.

FIG. 12 illustrates yet another exemplary head protection device 200 for protecting the face of a patient 502, which similarly to device 100 includes a shield 202 pivotally connected via a hinge 220 to a support platform 204. The device includes a vertical side wall 214 extending perpendicular from a base unit 212 and allowing a side pivotal opening of the shield 202. Optionally, the device 200 includes an adjuster unit (as shown in FIGS. 2-11) for allowing the adjustment of the distance of shield 202 from support platform 204.

Figure 13:
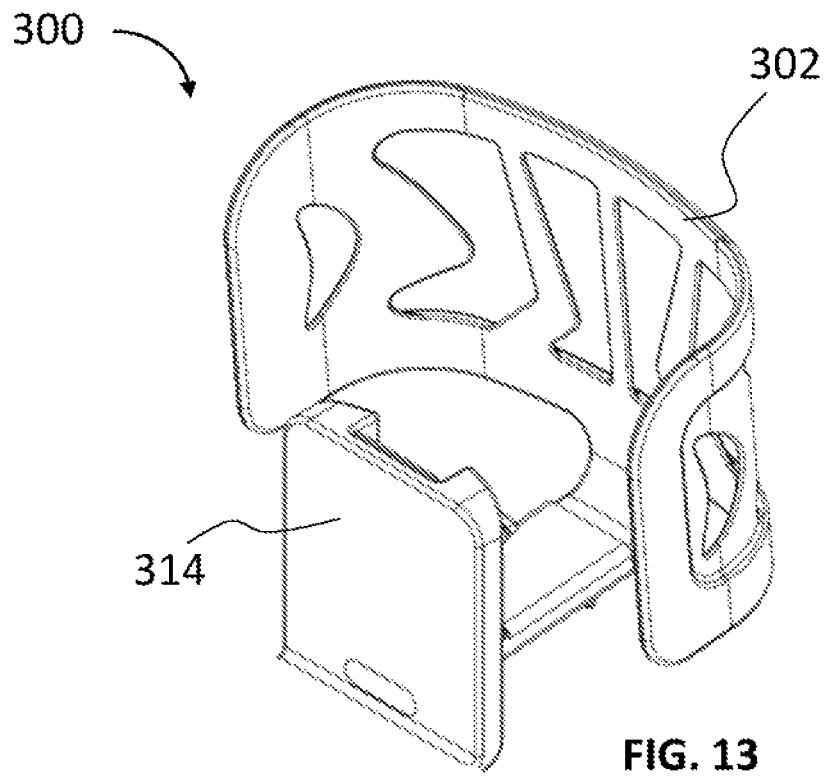
FIG. 13 illustrates a front perspective view of an exemplary head protection device with a head protection shield, according to some embodiments of the invention.
Figure 14:
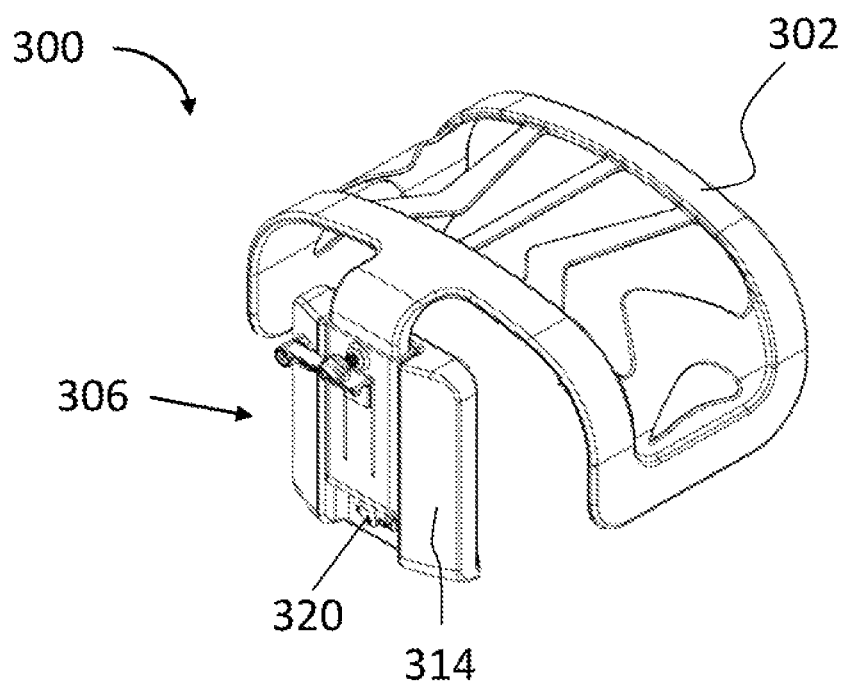
FIG. 14 illustrates a rear perspective view of the head protection device of FIG. 13, according to some embodiments of the invention.

FIGS. 13-14 illustrate yet another exemplary head protection device 300 for protecting the face of a patient, which is similar to device 100 with the exception that device 300 does not include a base unit (such as base unit 112 shown for example in FIG. 4). Device 300 includes a shield 302 pivotally connected via a hinge 320 to vertical rear wall 314. The device 300 includes an adjuster mechanism 306 which may be similar to adjuster mechanism 106 of device 100. Device 300 is connectable via attachment means, e.g., straps (not shown) to a patient bed/table/chair. In device 300, the patient positions his head on a head support platform (e.g., patient bed/chair/operation table) and the device is connected to the head support platform or an add-on system or a sub-system such to allow protection of a patient's upper body portion.

Figure 15:
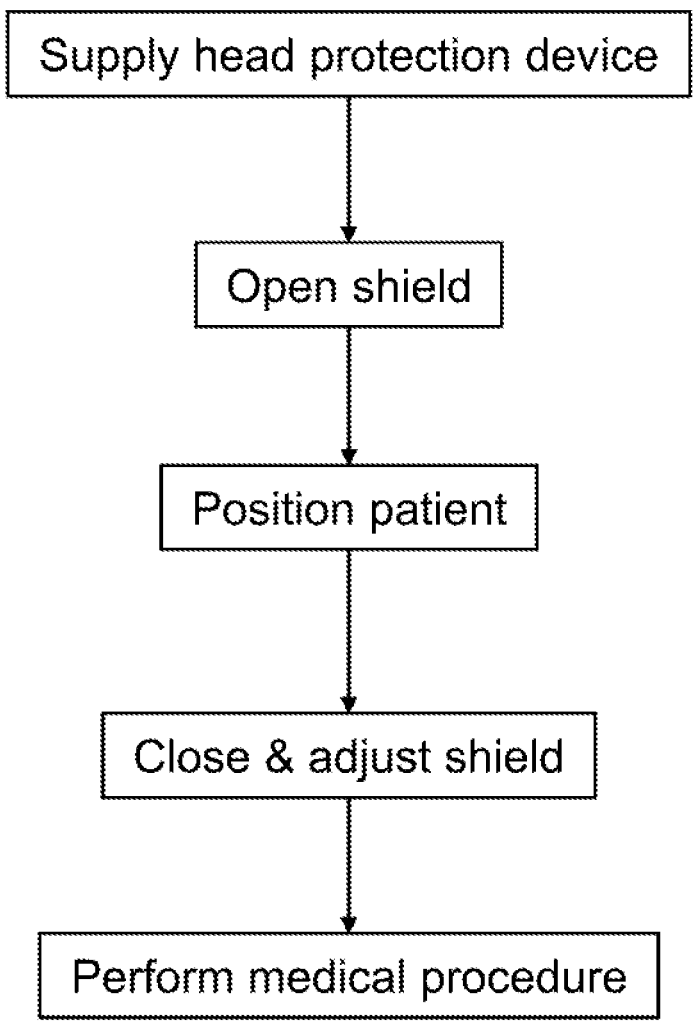
FIG. 15 is a flow chart illustration of a method of protecting a person positioned on a patient bed/table, according to some embodiments of the invention.

FIG. 15 is a flow chart illustration of a method of protecting a person positioned on a patient bed/table. For example, a head protection device, such as device 100, may include a shield, e.g., shield 102 positioned on a bed/table and/or on a patient support platform, e.g., support platform 104. Optionally, the device may be opened to facilitate positioning the patient on the support platform and/or closed to shield the patient while the patient is on the support platform. Optionally, the shield may be opened to facilitate the patient moving off the support platform. Alternatively, or additionally, the patient may position himself under or behind the shield without changing the shield's position. Once the patient is in position, the shield may be adjusted to shield the patient and/or for comfort of the patient and/or to allow access to the patient and/or to facilitate movement of the patient as necessary for a medical procedure. For example, the shield may provide collision protection to one or more parts of a patient.

For example, a face/head shield may be anchored onto a patient bed/table of an X-ray system. Optionally, the shield is opened, and/or the shield is optionally closed and/or adjusted. For example, the shield may be adjusted to be close to the face of the patient. For example, part of the shield and/or the entire shield/and/or the inner surface of the shield may be 0 to 2 cm distanced from the patients' face and/or 2 to 5 cm and/or 5 to 10 cm distanced from the patient. For example, adjusting the shield to be close to the patient may reduce the interference of the shield to positioning and/or movement of the C-arm or other X-ray equipment. Once the shield is in position, the X-ray system may be used to scan the patient and/or his face with reduced risk of collision with his face. Optionally, an x-ray system may visualize parts of the patient through the shield, for example the shield may be made of a radiolucent material with respect to the scanning radiation.

Optionally, the shield may be made of a material that is visible to an active collision avoidance system of the X-ray system or a portion thereof. It would be readily apparent to those skilled in the art that various materials such as radiolucent and carbon fibers may be envisioned without deviating from the scope of the present invention.

In some embodiments, a patient may be supported by a table and/or examination chair and/or bed/table and/or chair. Medical personnel may be using heavy and/or dangerous and/or moving equipment around the patient. For example, such a situation commonly occurs with X-ray systems having a moveable C-arm. Optionally the patient face/head shield includes a shield that protects sensitive parts of the patient from collisions. Optionally the shield is designed to allow access to the patient for a procedure.

In some embodiments, a face/head shield is mounted on a patient bed/table of an X-ray system. For example, the scanning equipment may include moving scanning elements. For example, the shield may be positioned over and/or around a face of a patient, for example to protect him from collision with the moving scanning equipment. Optionally, the shield may be made of radiolucent material and/or positioned close to and/or wrapped around the face of the patient for example to avoid interfering with movement and/or functioning of the X-ray system. Optionally the shield is configured to avoid irritating the patient. For example, a face/head shield may have large open spaces to avoid making the patient feel trapped and/or suffocated, and/or to protect the patient from possible collisions with an X-ray system or an X-ray add-on system.

As herein described, the device protection device includes a shield, for protecting a portion of a subject from a collision with an object moving relative to the subject and a support platform. Optionally, the device includes fixature means configured to hold the shield rigidly to a patient support device (e.g., patient bed/table) or to the support platform. For example, an adjustor may be positioned between the shield and the support platform. For example, the adjustor may allow movement of the shield with respect to the support platform, for example to facilitate positioning the patient on the support and/or to facilitate movement of the patient on the support platform. Optionally, the adjustment mechanism may be locked, for example holding the shield rigidly to the support for shielding the subject.

Each of the following terms: 'includes', 'including', 'has', 'having', 'comprises', and 'comprising', and, their linguistic, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof.

The term 'consisting essentially of' as used herein means that the scope of the claim is limited to the specified elements and those that do not materially affect the basic and novel characteristic(s) of the claimed device and materials.

Each of the phrases 'consisting of' and 'consists of', as used herein, means 'including and limited to'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably.

The term 'about', is some embodiments, refers to ±30% of the stated numerical value. In further embodiments, the term refers to ±20% of the stated numerical value. In yet further embodiments, the term refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub combination in the context or format of a single embodiment, may also be illustratively described and presented in the context or format of a plurality of separate embodiments.

Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A patient protection device for protecting a patient's head from collision with X-ray equipment, the device comprising:
   a rigid protector shield configured to at least partially cover the patient's face;
   a support platform having an upper surface configured to receive a back of the patient's head;
   a rear wall extending upwardly from a back edge of the support platform;
   a hinge for pivotably attaching the rigid protector shield to the rear wall, wherein the hinge is slidably positionable along a vertical length of the rear wall to vertically adjust a distance between the rigid protector shield and the upper surface of the support platform;
   wherein the rear wall comprises a hollow bracket having an opened top end and a bottom end;

wherein the rigid protector shield comprises an elongated rod; and wherein the hollow bracket is configured to receive the elongated rod via the open top end and to allow a vertical movement of the elongated rod within the hollow bracket.

2. The protection device of claim 1, wherein the rear wall comprises a groove and wherein the hollow bracket is configured to fit in the groove.

3. The protection device of claim 1, wherein the rigid protector shield further comprises side protection shields configured to protect sides of the patient's head.

4. The protection device of claim 3, wherein the rear wall and/or side protection shields comprise a radiation attenuating material for protecting medical personnel from scattered radiation in areas behind the patient's head.

5. The protection device of claim 4, wherein the radiation attenuating material is a metal selected from tungsten, lead, bismuth, antimony, barium, tantalum, and a combination thereof.

6. The protection device of claim 4, wherein the rear wall and/or side protection shields comprise layered material comprising one or more layers of a radiation attenuating material and one or more layers of a carbon fiber.

7. The protection device of claim 4, wherein the rear wall and/or side protection shields comprise a non-layered material comprising a thermoplastic material and a radiation attenuating material.

8. The protection device of claim 1, further comprising a stopper for locking the rigid protector shield to the rear wall and thereby preventing pivotal movement of the rigid protector shield with respect to the support platform.

9. The protection device of claim 1, wherein at least the rigid protector shield comprises a radiolucent material.

10. The protection device of claim 9, wherein the support platform comprises a radiolucent material.

11. The protection device of claim 1, wherein the rigid protector shield comprises a plurality of openings to allow comfort, relaxing and/or airy environment for the patient.

12. The protection device of claim 1, wherein the protector shield comprises carbon fibers.

13. The protection device of claim 1, wherein the support platform comprises carbon fibers.

14. The protection device of claim 1, further comprising attachment means to connect the shield and/or support platform to a sub-system, an add-on system, a patient table, a patient chair, and/or a patient bed.

15. The protection device of claim 1, further comprising a collision sensor configured in the shield to detect collisions.

16. The protection device of claim 1, further comprising a speaker configured in the shield to generate first audio signals.

17. The protection device of claim 16, further comprising a microphone configured in the shield to receive second audio signals.

18. The protection device of claim 1, further comprising a camera configured on the shield to capture visuals.

19. The protection device of claim 1, further comprising a display unit configured on the shield to display visual images.

20. The protection device of claim 19, further comprising a bi-directional communication unit to communicate audio signals over a communication network.

21. The protection device of claim 20, further comprising a battery to power the bi-directional communication unit or the display unit.

* * * * *